(12) United States Patent
Codd et al.

(10) Patent No.: US 6,562,865 B1
(45) Date of Patent: May 13, 2003

(54) COMPOSITION COMPRISING A TRAMADOL MATERIAL AND AN ANTICONVULSANT DRUG

(75) Inventors: Ellen E. Codd, Blue Bell, PA (US); Rebecca P. Martinez, Abington, PA (US); Kathryn E. Rogers, Audubon, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/634,904

(22) Filed: Aug. 9, 2000

Related U.S. Application Data

(60) Provisional application No. 60/150,201, filed on Aug. 20, 1999.

(51) Int. Cl.⁷ .......................... A61K 31/35; A61K 31/14
(52) U.S. Cl. ........................................ 514/456; 514/643
(58) Field of Search ................... 514/643, 456

(56) References Cited

U.S. PATENT DOCUMENTS 6,150,419 A * 11/2000 Fairbanks et al.
6,187,338 B1 * 2/2001 Caruso et al.

FOREIGN PATENT DOCUMENTS

| WO | WO 9606822 A1 | 3/1996 |
| WO | WO 9806708 A1 | 2/1998 |
| WO | PCT/US00/21622 | 9/2000 |

OTHER PUBLICATIONS

Rost et al., The effect of tramadol and other analgesics on the pain . . . , abstract, Arzneim.–Forsch. 1978, vol. 28(1a0, pp. 181–183.*
Dressler et al., Benzodiazepine in geriatric patients . . . , abstract, Anaesthesiologie und reanimation, 1996, vol. 21/5, pp. 136–138.*
Kralinsky et al., Tramal in the treatment of pain in children . . . , abstract, Klinicka Onkologie, 1994, col. 7/6, pp. 182–185.*
K. Kralinsky E.A.:" Tramal in the treatment of pain in children with malignancies" XP002162259 abstract & Klinicka Onkologie, vol. 7, No. 6, 1994, pp. 182–185.
S. Grond, T. Meuser: "ek opiods–an educational substitute for morphine?" Current Opinion in Anaesthesiology, vol. 11, No. 5, 1998, pp. 559–565 XP000982759.

* cited by examiner

*Primary Examiner*—Marianne C. Seidel
*Assistant Examiner*—Vickie Kim

(57) ABSTRACT

This invention relates to a pharmaceutical composition comprising a combination of a tramadol material and an anticonvulsant drug and to the pharmacological use of the composition in treating conditions of pain and neurologic or psychiatric disorders. The composition produces a combination product having improved properties, requiring less of each ingredient and producing a synergistic effect.

11 Claims, 3 Drawing Sheets

COMPOSITION COMPRISING A TRAMADOL MATERIAL AND AN ANTICONVULSANT DRUG

This application claims benefit of No. 60/150,201 filed Aug. 20, 1999.

FIELD OF THE INVENTION

The present invention is directed to a pharmaceutical composition useful in the treatment of pain. More particularly, this invention is directed to a pharmaceutical composition comprising a combination of a tramadol material and an anticonvulsant drug.

BACKGROUND OF THE INVENTION

Throughout this disclosure, various publications are cited and are herein incorporated by reference to describe more fully the state of the art to which this invention pertains.

U.S. Pat. No. 3,652,589 discloses a class of analgesic cycloalkanol-substituted phenol esters having a basic amine group in the cycloalkyl ring. The compound (1R,2R or 1S,2S)-2-[(dimethylamino)methyl]-1-(3-methoxyphenyl) cyclohexanol, commonly known as tramadol, is specifically disclosed therein. A series of articles pertaining to the pharmacology, toxicology and clinical studies of tramadol are found in Arzneim. Forsch., (Drug Res.), 1978, 28(I), 114. Tramadol produces its analgesic effect through a mechanism that is neither fully opioid-like nor non-opioid-like (Driessen, et al., *Arch. Pharmacol.,* 1990, 341, R104). The Abstracts of the VI$^{th}$ World Congress on Pain, Apr. 1–6 (1990), disclose that tramadol hydrochloride is an orally active pure agonist opioid analgesic. However, clinical experience indicates that tramadol lacks many of the typical side effects of opioid agonists, e.g., respiratory depression (W. Vogel et al., *Arzneim. Forsch.,* (Drug Res.), 1978, 28(I), 183), constipation (I. Arend et al., *Arzneim. Forsch.,* (Drug Res.), 1978, 28(I), 199), tolerance (L. Flohe et al., *Arzneim. Forsch.,* (Drug Res.), 1978, 28(I), 213) and abuse liability (T. Yanagita, *Arzneim. Forsch.,* (Drug Res.), 1978, 28(I), 158). When given at a dose of 50 mg by rapid i.v. injection, tramadol may produce certain side effects unique to tramadol including hot flushes and sweating. Despite these side effects, tramadol's 'atypical' combination of non-opioid and opioid activity makes tramadol a very unique drug. Tramadol is currently marketed as an analgesic.

Opioids have for many years been used as analgesics to treat severe pain. They, however, produce undesirable side effects and, as a result, cannot always be given repeatedly or at high doses. The side effect problems are well documented in the literature. See, for example, T. Reisine and G. Pasternak in "Goodman and Gilman's, The Pharmacological Basis of Therapeutics", 9th edition; Hardman et al.; McGraw-Hill, New York, 1996; Chapter 23; pages 521–555 wherein it is disclosed that morphine and its congeners, e.g., codeine, hydrocodone and oxycodone are opioid agonist analgesics that exhibit side effects such as respiratory depression, constipation, tolerance and abuse liability.

To reduce the side effect problems of opioids, opioids have been combined with other drugs, including non-opioid analgesic agents, which lower the amount of opioid needed to produce an equivalent degree of analgesia. It has been claimed that some of these combination products also have the advantage of requiring less of each ingredient while producing a synergistic analgesic effect. Compositions including combinations of opioid analgesics with drugs other than analgesics exhibit a variety of effects, i.e., sub-additive (inhibitory), additive or superadditive (A. Takemori, *Annals New York Acad. Sci.,* 1976, 281, 262). A combination of morphine and methadone, another opioid analgesic, exhibits an additive effect (R. Taber, et al., *J. Pharm. Expt. Thera.,* 1969,169(1), 29). U.S. Pat. No. 4,571, 400 discloses that the combination of dihydrocodeine, an opioid analgesic, and ibuprofen, a non-opioid analgesic, provides superadditive effects when the components are within certain ratios. See also, U.S. Pat. Nos. 4,587,252 and 4,569,937 which disclose other ibuprofen opioid combinations. Superadditive analgesia with a 1:125 mixture of butorphanol:acetaminophen (an opioid analgesic combined with a non-opioid analgesic) has been reported, whereas a 1:10 mixture did not show any statistically significant superadditive analgesia (A. Pircio, et al., *Arch. Int. Pharmacodyn.,* 1978, 235,116).

As an analgesic, tramadol has been combined with both opioid and non-opioid analgesic drugs. Such compositions have exhibited synergistic effects in treating pain while using less of each ingredient to produce an equivalent degree of analgesia. Specifically, U.S. Pat. No. 5,516,803 discloses the composition of tramadol and a NSAID, particularly ibuprofen. U.S. Pat. No. 5,468,744 discloses tramadol plus any of oxycodone, codeine or hydrocodone and U.S. Pat. No. 5,336,691 discloses tramadol in combination with acetaminophen.

As a class, anticonvulsant drugs are not known to be useful in the treatment of pain. However, certain anticonvulsant drugs have been found useful in the treatment of neuropathic pain. U.S. Pat. No. 4,513,006 discloses a class of anticonvulsant drugs including the 2,3,4,5-bis-O-(1-methylethylidene)-β-D-fructopyranose sulfamates known as topiramate. U.S. Pat. No. 5,760,007, which is herein incorporated by reference, further discloses topiramate as useful for the treatment of neuropathic pain.

In addition, anticonvulsant drugs have been combined with non-toxic blockers for the N-methyl-d-aspartate (NMDA) receptor. Such compositions have been described as useful in the treatment of neuropathic pain. For example, WO 98/07447 broadly discloses the combination of a neuropathic pain alleviating amount of an anticonvulsant drug, including gabapentin, lamotrigine, valproic acid, topiramate, famotidine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan or L-5-hydroxytrytophan and an anticonvulsant potentiating amount of a non-toxic blocker for the NMDA receptor. This reference, however, does not teach the synergistic composition of the present invention.

Anticonvulsant drugs combined with NSAIDS or narcotic analgesics have also been described as useful in the treatment of pain. WO 99/12537 discloses a composition of the anticonvulsant compounds gabapentin or pregabalin in combination with the NSAID naproxen or with narcotic analgesics. Combinations of anticonvulsants and other drugs with opioid analgesics have been suggested (Donnadieu, S., et al., Pain Relief, *Presse Medicale,* 1998, 27/39, 2062–2069). These references, however, also do not teach the synergistic composition of the present invention.

Heretofore, no reference has disclosed a pharmaceutical composition comprising a combination of the centrally acting analgesic tramadol and an anticonvulsant drug demonstrating that such a composition has a synergistic effect while using less of each ingredient for treating conditions of pain and neurological or psychiatric disorders in mammals.

Therefore, it is an object of the present invention to produce a combination product with a tramadol material having improved properties. It is also an object of the present invention to produce a combination product with a tramadol material and an anticonvulsant drug wherein the combination has a synergistic effect while using less of each ingredient. It is another object of the present invention to produce a combination product with tramadol hydrochloride and an anticonvulsant drug selected from, but not limited to, topiramate, gabapentin, lamotrigine or RWJ-333369; wherein the combination has a synergistic effect while using less of each ingredient. A further object of the present invention is to provide a method for treating conditions of pain and neurological or psychiatric disorders in mammals.

SUMMARY OF THE INVENTION

Briefly, according to the present invention, there is provided a pharmaceutical composition comprising a combination of a tramadol material and an anticonvulsant drug, wherein the tramadol material and the anticonvulsant drug are present in a ratio based on a fraction of their respective 50% effective dose ($ED_{50}$) values, which ratio is from about 1:1 to about 300:1 or from about 1:1 to about 1:300.

An embodiment of the pharmaceutical composition of the present invention comprises a combination of a tramadol material and an anticonvulsant drug, wherein the tramadol material and the anticonvulsant drug are present in a ratio based on a fraction of their respective $ED_{50}$ values, which ratio is from about 1:1 to about 100:1 or from about 1:1 to about 1:100.

Another embodiment of the pharmaceutical composition of the present invention comprises a combination of a tramadol material and an anticonvulsant drug, wherein the tramadol material and the anticonvulsant drug are present in a ratio based on a fraction of their respective $ED_{50}$ values, which ratio is from about 1:1 to about 30:1 or from about 1:1 to about 1:30.

The pharmaceutical composition of the present invention is exemplified by a combination of a tramadol material and the anticonvulsant drug topiramate, wherein the tramadol material and topiramate are present in a ratio based on a fraction of their respective $ED_{50}$ values, which ratio is from about 1:1 to about 20:1.

The pharmaceutical composition of the present invention is also exemplified by a combination of a tramadol material and the anticonvulsant drug gabapentin, wherein the tramadol material and gabapentin are present in a ratio based on a fraction of their respective $ED_{50}$ values, which ratio is from about 2:1 to about 20:1.

The pharmaceutical composition of the present invention is further exemplified by a combination of a tramadol material and the anticonvulsant drug lamotrigine, wherein the tramadol material and lamotrigine are present in a ratio based on a fraction of their respective $ED_{50}$ values, which ratio is from about 1:2 to about 1:8.

The pharmaceutical composition of the present invention is still further exemplified by a combination of a tramadol material and the anticonvulsant drug RWJ-333369, wherein the tramadol material and RWJ-333369 are present in a ratio based on a fraction of their respective $ED_{50}$ values, which ratio is from about 1:1 to about 20:1 or from about 1:1 to about 1:20.

The present invention also provides a method for treating a condition of pain or a neurological or psychiatric disorder in a mammal in need thereof comprising administering to the mammal a therapeutically effective dose of a pharmaceutical composition for treating the condition of pain or the neurological or psychiatric disorder comprising a combination of a tramadol material and an anticonvulsant drug, wherein the tramadol material and the anticonvulsant drug are present in a ratio based on a fraction of their respective $ED_{50}$ values, which ratio is from about 1:1 to about 300:1 or from about 1:1 to about 1:300.

An embodiment of the method of the present invention comprises administering a therapeutically effective dose of a pharmaceutical composition comprising a combination of a tramadol material and an anticonvulsant drug, wherein the tramadol material and the anticonvulsant drug are present in a ratio based on a fraction of their respective $ED_{50}$ values, which ratio is from about 1:1 to about 100:1 or from about 1:1 to about 1:100.

Another embodiment of the method of the present invention comprises administering a therapeutically effective dose of a pharmaceutical composition comprising a combination of a tramadol material and an anticonvulsant drug, wherein the tramadol material and the anticonvulsant drug are present in a ratio based on a fraction of their respective $ED_{50}$ values, which ratio is from about 1:1 to about 30:1 or from about 1:1 to about 1:30.

The method of the present invention is exemplified by administering a therapeutically effective dose of the pharmaceutical composition comprising a combination of a tramadol material and the anticonvulsant drug topiramate, wherein the tramadol material and topiramate are present in a ratio based on a fraction of their respective $ED_{50}$ values, which ratio is from about 1:1 to about 20:1.

The method of the present invention is also exemplified by administering a therapeutically effective dose of the pharmaceutical composition comprising a combination of a tramadol material and the anticonvulsant drug gabapentin, wherein the tramadol material and gabapentin are present in a ratio based on a fraction of their respective $ED_{50}$ values, which ratio is from about 2:1 to about 20:1.

The method of the present invention is further exemplified by administering a therapeutically effective dose of the pharmaceutical composition comprising a combination of a tramadol material and the anticonvulsant drug lamotrigine, wherein the tramadol material and lamotrigine are present in a ratio based on a fraction of their respective $ED_{50}$ values, which ratio is from about 1:2 to about 1:8.

The method of the present invention is still further exemplified by administering a therapeutically effective dose of the pharmaceutical composition comprising a combination of a tramadol material and the anticonvulsant drug RWJ-333369, wherein the tramadol material and RWJ-333369 are present in a ratio based on a fraction of their respective $ED_{50}$ values, which ratio is from about 1:1 to about 20:1 or from about 1:1 to about 1:20.

DETAILED DESCRIPTION OF THE INVENTION

Figure 1:
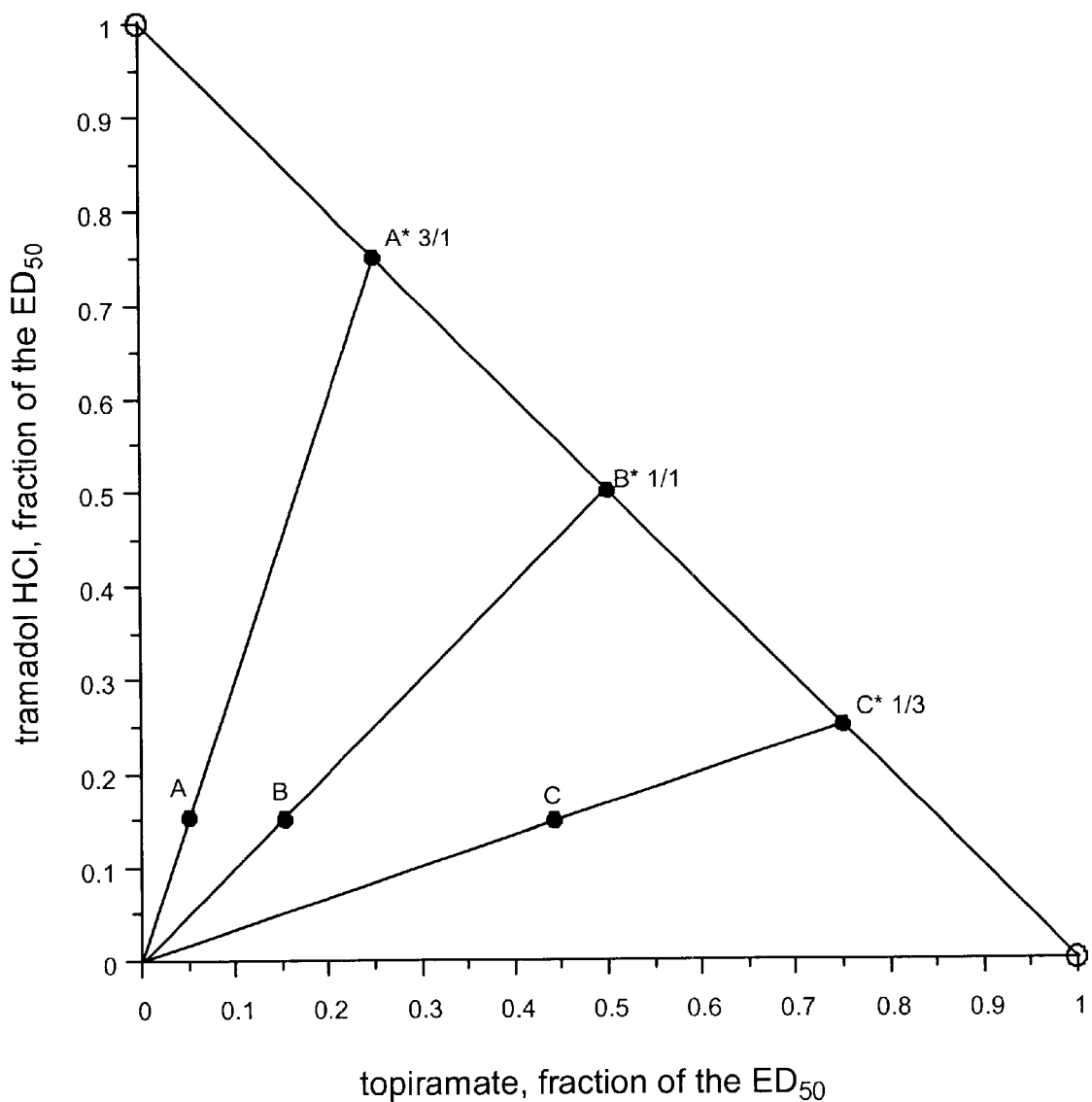
FIG. 1 is an isobologram showing the antiallodynic effect of certain combinations of tramadol hydrochloride and topiramate in rats using the Chung Model. The dose level for each component of each combination is expressed as the fraction of its $ED_{50}$ value.

The tramadol material is any one of (1R,2R or 1S,2S)-2-[(dimethylamino)methyl]-1-(3-methoxyphenyl)-cyclohexanol (tramadol), its N-oxide derivative ("tramadol N-oxide"), and its O-desmethyl derivative ("O-desmethyl tramadol") or mixtures thereof. It also includes the individual stereoisomers, mixtures of stereoisomers, including the racemates, pharmaceutically acceptable salts of the amines, such as the hydrochloride salt, solvates and polymorphs of the tramadol material. Tramadol is commercially available from Grunenthal or may be made by the process described in U.S. Pat. No. 3,652,589, which is herein incorporated by reference.

Tramadol N-oxide is prepared by treating tramadol as a free base with an oxidizing agent, e.g., hydrogen peroxide (30%), in an organic solvent, e.g., methanol or isopropanol, with, but preferably without heating. See, "Reagents For Organic Synthesis", 1, 471, Fieser & Fieser eds., Wiley N.Y.; (1987) and B. Kelentey et al., *Arzneim. Forsch.*, 1957, 7, 594. With heating, the reaction takes about 1 h, whereas without heating the reaction takes about 3 days. Following the oxidation, the mixture is treated with an agent, e.g. $PtO_2$ or preferably Pt/C, for about a day, to destroy the excess hydrogen peroxide. The mixture is filtered, followed by the evaporation of the filtrate and then the residue is recrystallized from an organic solvent mixture, e.g., methylene chloride/ethyl acetate.

O-desmethyl tramadol is prepared by treating tramadol as a free base under O-demethylating reaction conditions, e.g., reacting it with a strong base such as NaOH or KOH, thiophenol and diethylene glycol (DEG) with heating to reflux (Wildes, et al., *J. Org. Chem.*, 1971, 36, 721). The reaction takes about 1 h, followed by cooling and then quenching in water of the reaction mixture. The quenched mixture is acidified, extracted with an organic solvent such as ethyl ether, basified and then extracted with a halogenated organic solvent such as methylene chloride. The extract is then dried and the solvent evaporated to yield the O-desmethyl product, which may then be short-path distilled, converted to its corresponding salt, e.g., treated with an acidified (HCl/ethanol) solution, and recrystallized from an organic solvent mixture, e.g., ethanol/ethyl ether.

Anticonvulsant drugs, according to the scope of the present invention, are effective antiepileptic compounds some of which have been described as useful for the treatment of neuropathic pain and include, without limitation, topiramate, RWJ-333369, gabapentin, lamotrigine, pregabalin, carbamazepine, phenytoin, fosphenytoin, mephenytoin, ethotoin, valproic acid, famotidine, phenobarbital, mephobarbital, metharbital, diphenylhydantoin, primidone, ethosuximide, methsuximide, phensuximide, trimethadione, benzodiazepine, phenacemide, acetazolamide, progabide, clonazepam, divalproex sodium, magnesium sulfate injection, paramethadione, phenytoin sodium, valproate sodium, clobazam, sulthiame, dilantin, diphenylan or L-5-hydroxytrytophan, salts thereof, complexes thereof and mixtures of any of the foregoing.

The anticonvulsant drug topiramate is any one of the 2,3,4,5-bis-O-(1-methylethylidene)-β-D-fructopyranose sulfamates, its derivatives or mixtures thereof. It also includes the individual stereoisomers, mixtures of stereoisomers, including racemates thereof, e.g., the various α and β attachments, i.e., above and below the plane of the 6-membered ring structure, pharmaceutically acceptable salts, such as the hydrochloride salt, solvates and polymorphs of the topiramate material. Topiramate is commercially available from Ortho Pharmaceutical Corporation or may be made by the process described in U.S. Pat. No. 4,513,006, which is herein incorporated by reference.

RWJ-333369 is disclosed in U.S. Pat. No. 5,698,588 and described as useful in the treatment of central nervous system disorders, especially as anticonvulsants, antiepileptics, neuroprotective agents and centrally acting muscle relaxants. RWJ-333369 is further described by the Chemical Abstracts Service (CAS) Index Name 1,2-ethanediol, 1-(2-chlorophenyl)-, 2-carbamate, (S)- and CAS Registry Number 194085-75-1.

In the pharmaceutical composition of the present invention, the portion of the composition that is an anticonvulsant drug may be either topiramate, gabapentin, lamotrigine, RWJ-333369, another anticonvulsant drug or a combination of topiramate and, without limitation, one or more of another anticonvulsant drug. It is intended that a pharmaceutical composition comprising the combination of a tramadol material and an anticonvulsant drug as the active ingredients in synergistic ratios based on a fraction of their respective $ED_{50}$ values as well as methods of preparing the instant composition in synergistic ratios are also encompassed within the present invention.

In a pharmaceutical composition of the present invention, a tramadol material and an anticonvulsant drug are present in a ratio based on a fraction of their respective $ED_{50}$ values which ratio may vary from about 1:1 to about 300:1 or, reversibly, from about 1:1 to about 1:300; preferably, from about 1:1 to about 100:1 or from about 1:1 to about 1:100; and, more preferably, from about 1:1 to about 30:1 or from about 1:1 to about 1:30, depending upon the desired result. An instant composition may comprise, for example, a combination of a tramadol material and the anticonvulsant drug topiramate, wherein the tramadol material and topiramate are present in a ratio based on a fraction of their respective $ED_{50}$ values, which ratio is from about 1:1 to about 20:1; preferably, from about 1.5:1 to about 10:1; and, more preferably, from about 3:1 to about 5:1. An instant composition may also comprise a combination of a tramadol material and the anticonvulsant drug gabapentin, wherein the tramadol material and gabapentin are present in a ratio based on a fraction of their respective $ED_{50}$ values, which ratio is from about 2:1 to about 20:1; and, preferably, from about 9:1 to about 15:1. An instant composition may further comprise a combination of a tramadol material and the anticonvulsant drug lamotrigine, wherein the tramadol material and lamotrigine are present in a ratio based on a fraction of their respective $ED_{50}$ values, which ratio is from about 1:2 to about 1:8; and, preferably, about 1:3. An instant composition may still further comprise a combination of a tramadol material and the anticonvulsant drug RWJ-333369, wherein the tramadol material and RWJ-333369 are present in a ratio based on a fraction of their respective $ED_{50}$ values, which ratio is from about 1:1 to about 20:1 or from about 1:1 to about 1:20; preferably, from about 1:1 to about 10:1 or from about 1:1 to about 1:10; and, more preferably, from about 1:1 to about 4:1 or from about 1:1 to about 1:4. Compositions comprising a combination of a tramadol material and an anticonvulsant drug within these ratios exhibit synergistic effects. A pharmaceutical composition according to the present invention comprises a therapeutically effective dose of a tramadol material for treating a condition of pain or a neurological or psychiatric disorder in a mammal in need thereof in combination with an anticonvulsant drug. Preferably, the instant composition comprises a combination of tramadol hydrochloride and an anticonvulsant drug selected from topiramate, gabapentin, lamotrigine or RWJ-333369.

Pharmaceutical compositions comprising a combination of a tramadol material and the anticonvulsant drug as the active ingredients in an intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in an oral dosage form, any of the usual pharmaceutical media may be employed. For example, in the case of oral liquid preparations (such as suspensions, elixirs and solution), water, glycols, oils, alcohols, flavoring agents, preservatives, coloring agents and the like may be used. In the case of oral solid preparations (such as, for example, powders, capsules and tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. In the case wherein one or more other pharmaceutically active components are added to the composition combining a tramadol material and an anticonvulsant drug, those components may be added in amounts known in the art and may be given at dosages conventional for such components. The pharmaceutical compositions of the present invention will generally be in the form of a dosage unit, e.g., tablet, capsule, powder, injection, teaspoonful and the like, wherein the preferred amount of each of the active ingredient to be contained therein is determined by the aforementioned ratios.

The dosage unit is calculated based on the amount of active ingredient which may be given to a 70 kg human subject in a single dose. An instant pharmaceutical composition may be given at a daily dose of from about 5 mg/day to about 8000 mg/day. However, it will be appreciated that the precise therapeutically effective dose of the active ingredients will vary depending upon the relative amount of each active component being used, upon the particular tramadol material and anticonvulsant drug being used and upon the aforementioned synergistic ratios. A single dose of a formulation of a pharmaceutical composition demonstrating synergistic activity, therefore, may contain a therapeutically effective dose of active ingredient of from about 20 mg to about 400 mg of a combination of a tramadol material and an anticonvulsant drug; preferably, from about 20 mg to about 200 mg; more preferably, from about 20 mg to about 100 mg; and, most preferably, from about 20 mg to about 50 mg. Thus, for example, a 20 mg formulation of a pharmaceutical composition comprising a synergistic combination of a tramadol material and the anticonvulsant drug topiramate, wherein the tramadol material and topiramate are present in a ratio based on a fraction of their respective $ED_{50}$ values, which ratio is about 3:1 will contain about 15 mg of a tramadol material and about 5 mg of topiramate. Furthermore, the tramadol material and an anticonvulsant drug need not be present in the same formulation to achieve the results described herein. They may be administered individually at about the same time or in a single tablet. Advantageously, a pharmaceutical composition of the present invention may be administered in a single daily dose or the total daily dose may be administered in divided doses of two, three or four times daily. Optimal therapeutically effective doses to be administered may be readily determined by those skilled in the art, will vary with the particular combination of a tramadol material and an anticonvulsant drug used, the amount of active ingredients used in a synergistic ratio based on a fraction of their respective $ED_{50}$ values, the strength of the preparation, the mode of administration and the advancement of the condition or disorder treated. In addition, factors associated with the particular subject being treated, including subject age, weight, diet and time of administration, will result in the need to adjust the dose to an appropriate therapeutically effective level.

The pharmaceutical compositions of the present invention are useful for treating conditions of pain and certain neurological and psychiatric disorders in mammals by the administration of a composition comprising a combination of a tramadol material and an anticonvulsant drug. Those skilled in the art of treating mammalian pain know that the types of pain experienced by mammals are varied. Examples of conditions of mammalian pain include, but are not limited to, centrally mediated pain, peripherally mediated pain, structural or soft tissue injury related pain, progressive disease related pain and neuropathic pain states, all of which would include acute pain such as caused by acute injury, trauma or surgery; chronic pain such as caused by neuropathic conditions, diabetic peripheral neuropathy, post-herpetic neuralgia, trigeminal neuralgia, post-stroke pain syndromes or cluster or migraine headaches; and inflammatory condition pain such as caused by osteoarthritis, rheumatoid arthritis or as sequela to disease, acute injury or trauma. The composition of the present invention is also useful in the treatment of certain neurological and psychiatric disorders including, but not limited to, bipolar disorder, psychosis, post-traumatic stress disorder, social phobia, obsessive-compulsive disorder; movement disorders such as akathisia, restless leg syndrome, tardive dyskinesia or central tremor; neurodegeneration in diseases such as ischemias (acute, delayed, recovery) or degeneration of nervous system cells due to Alzheimer's disease, Parkinson's disease or surgery; particularly, open-chest surgery; and, more particularly, open-heart or bypass surgery.

EXPERIMENTAL EXAMPLES

The following experimental examples describe the composition comprising a combination of a tramadol material and an anticonvulsant drug in greater particularity and are intended to be a way of illustrating but not limiting the invention.

General Method A
Procedure for Testing the Antiallodynic Effect of the Composition The procedure used to detect and compare the synergistic effect of the composition of the present invention for which there is a good correlation with human efficacy for the treatment of pain is the procedure for the measurement of allodynia found in the Chung Model (Chaplan S. R., Bach F. W., Pogrel J. W., Chung J. M. and Yaksh T. L., Quantitative Assessment of Tactile Allodynia in the Rat Paw, *J. Neurosci. Meth.*, 1994, 53, 55–63 and Kim S. H. and Chung J. M., An Experimental Model for Peripheral Neuropathy Produced by Segmental Spinal Nerve Ligation in the Rat, *Pain*, 1992, 50, 355–363). The antiallodynic effect of the composition of the present invention in the Chung Model is expressed in % MPE (Maximum Possible Effect).

Animals

Pathogen-free, male albino Sprague-Dawley rats, 200 g, were purchased from Harlan Industries (Indianapolis, Ind.) and maintained on a 12-h light/dark cycle (lights on at 06:00 h) in a climate-controlled room with food and water available ad libitum.

Surgical Procedure and Measurement of Allodynia

The rats were anesthetized with isoflurane inhalant anesthesia. The left lumbar spinal nerve at the level of L5 was tightly ligated (4-0 silk suture) distal to the dorsal root ganglion and prior to entrance into the sciatic nerve, as described by Kim and Chung. The incisions were closed and the rats were allowed to recover under conditions described above. This procedure results in mechanical allodynia in the left hind paw. The sham operation, when performed, consisted of a similar surgical procedure lacking only the final ligation of the spinal nerve. Mechanical (tactile) allodynia was assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test (Chaplan, et al). Normal rats, sham operated rats, and the contralateral paw of L5 ligated rats withstand at least 148.1 mN (equivalent to 15 g) of pressure without responding. Spinal nerve ligated rats respond to as little as 4.0 mN (equivalent to 0.41 g) of pressure on the affected paw. Rats were included in the study only if they did not exhibit motor dysfunction (e.g., paw dragging or dropping) and their PWT was below 39.2 mN (equivalent to 4.0 g).

Preparation of the Composition Doses of a Tramadol Material and an Anticonvulsant Drug The dosing materials were all prepared in the vehicle, a suspension of 0.5% hydroxypropyl methylcellulose in distilled water; drug weights were calculated as the free base. The tramadol solution was prepared first, and the appropriate volume of this solution was added to a neat amount of the anticonvulsant to give the final dosing suspension. Drug weights were calculated as the free base, and the ratios used were based on the respective $ED_{50}$ values of tramadol and the anticonvulsant. The necessary doses for each ratio were prepared separately and dosed orally in a volume of 10 mL/kg per rat.

Animal Dosing

The Chung Model rats were all dosed orally with the composition comprising a combination of tramadol hydrochloride (calculated as the base) and the anticonvulsant drug (calculated as the base) or the composition of each agent separately dissolved in distilled water or dissolved in a suspension of 0.5% hydroxypropyl methylcellulose in distilled water. The dosing volume was 10 mL/kg.

The rats were intubated with various doses of tramadol hydrochloride alone, anticonvulsant drug alone, combined doses of tramadol hydrochloride and anticonvulsant or vehicle such as distilled water or a suspension of 0.5% hydroxypropyl methylcellulose in distilled water.

Analysis of Antiallodynic Effect

Within a certain time after the oral administration of tramadol hydrochloride alone, the anticonvulsant drug alone, the composition comprising a combination of tramadol hydrochloride and the anticonvulsant drug or vehicle alone, the PWT test was commenced. Each rat was used in the evaluation of only a single dose-ratio.

The analysis of possible synergistic effect for the compositions at each fixed ratio was determined (R. J. Tallarida, et al., *Life Sci.*, 1989, 45, 947). This procedure involves the determination of the total amount in the mixture that is required to produce a specified synergistic antiallodynic effect at the 50% dose level (that is, the $ED_{50mix}$ or $Z_{mix}$) and the corresponding total amount that would be expected under simple additivity ($ED_{50add}$ or $Z_{add}$). Where it is established that $Z_{mix} < Z_{add}$ for a specific fixed-ratio, then that composition has a synergistic antiallodynic effect. Both the quantities $ED_{50mix}$ and $ED_{50add}$ are random variables. $ED_{50mix}$ was determined from the dose-response curve for a specific fixed-ratio of the components; $ED_{50add}$ was calculated from the $ED_{50}$ values for the individual drugs. $Z_{mix}$ was then compared to $Z_{add}$ via a Student's t-test.

The interaction between tramadol hydrochloride and the anticonvulsant drug was determined at precise ratios of tramadol hydrochloride and the anticonvulsant drug. Multiple (typically 4–6) coded doses of each selected combination were studied for synergistic antiallodynic effect using an experimental design which permitted the complete randomization of the separate dosage forms tested.

Example A1

Synergistic Effect of the Tramadol/Topiramate Composition

The interaction of selected, precise ratios based on a fraction of the $ED_{50}$ values of tramadol hydrochloride and topiramate for each ratio dosed in the Chung model are shown by the data in Table 1 and illustrated in the isobologram in FIG. 1.

In FIG. 1, the fraction of the $ED_{50}$ values for the individual drugs alone lie on their respective axes. For example, the $ED_{50}$ value of tramadol alone at 2 hours post-dosing was 94.47 mg/kg and is illustrated in FIG. 1 at the value of 1. The $ED_{50}$ value of topiramate alone at 2 hours post-dosing was 98.04 mg/kg and is illustrated in FIG. 1 at the value of 1. Therefore, the line joining the $ED_{50}$ value of the two separate drugs represents the calculated simple additivity of the antiallodynic effect at different ratios.

Accordingly, for each combination studied, the point at the asterisked letter (e.g., A*) represents the theoretical additive $ED_{50}$ value ($Z_{add}$) for a particular dose ratio. Further, the points labeled A, B and C represent the actual, experimentally determined fraction of the $ED_{50}$ values ($Z_{mix}$) for the tramadol hydrochloride and topiramate combinations in the ratios of 3:1, 1:1 and 1:3, respectively.

Each of the fixed ratio combinations tested revealed significant antiallodynic synergism (using the Student's t-test at the points A and B, 0.01 level and at point C, 0.05 level). Thus, the synergy is pronounced (e.g., the $Z_{add}/Z_{mix}$ ratio for A*/A was 4.87 and for C*/C was 1.69) and was observed over a wide range of dose ratios.

TABLE 1

Tramadol:Topiramate Chung Model Data

| ED$_{50}$ value ratios (tramadol: topiramate) | TRAMADOL: TOPIRAMATE DRUG COMBINATIONS Dose (mg/kg, p.o.) | | | % MPE | ED$_{50}$ (SEM[1]) or Z value (SEM) at 2 hours | |
|---|---|---|---|---|---|---|
| | Tramadol | Topiramate | Total Dose | | $Z_{mix}$ (SEM) | $Z_{add}$ (SEM) |
| Tramadol only | 50 | | | 3.77 | 94.47 (5.27)[2] | |
| | 75 | | | 20.62 | | |
| | 100 | | | 45.38 | | |
| | 125 | | | 74.29 | | |
| | 150 | | | 100 | | |
| 0.75:0.25 | 8.86 | 3.06 | 11.92 | 30.54 | 19.6 (5.64) | 95.36 (4.3) |
| | 17.71 | 6.13 | 23.84 | 50.76 | | |
| | 35.43 | 12.26 | 47.68 | 90.93 | | |
| | 70.85 | 24.51 | 95.36 | 95.53 | | |
| | 141.7 | 49.02 | 190.73 | 100 | | |
| 0.52:0.48 | 6.13 | 5.90 | 12.03 | 23.84 | 28.50 (1.83) | 96.2 (4.2) |
| | 12.25 | 11.81 | 24.06 | 39.32 | | |
| | 24.51 | 23.62 | 48.13 | 68.22 | | |
| | 49.02 | 47.24 | 96.26 | 92.70 | | |
| 0.25:0.75 | 1.48 | 4.60 | 6.07 | 4.97 | 57.4 (9.57) | 97.15 (5.2) |
| | 2.95 | 9.19 | 12.14 | 13.82 | | |
| | 5.90 | 18.38 | 24.29 | 28.72 | | |
| | 11.81 | 36.77 | 48.57 | 34.55 | | |
| | 23.62 | 73.53 | 97.15 | 58.85 | | |
| | 47.24 | 147.06 | 194.3 | 88.30 | | |
| Topiramate only | | 25 | | 11.54 | 98.04 (6.75)[2] | |
| | | 50 | | 26.58 | | |
| | | 100 | | 56.42 | | |
| | | 250 | | 76.51 | | |
| | | 500 | | 94.38 | | |

[1]SEM = standard error of the mean
[2]Represents ED$_{50}$ value of drug alone

Example A2

Synergistic Effect of the Tramadol/Gabapentin Composition

The interaction of selected, precise ratios based on a fraction of the ED$_{50}$ values of tramadol hydrochloride and gabapentin for each ratio dosed in the Chung model are shown by the data in Table 2. The fixed ratio combination 9:1 revealed significant antiallodynic synergism (p<0.05).

TABLE 2

Tramadol:Gabapentin Chung Model Data

| ED$_{50}$ value ratios (tramadol: gabapentin) | TRAMADOL: GABAPENTIN DRUG COMBINATIONS Dose (mg/kg, p.o.) | | | Chung Model | ED$_{50}$ (SEM[1]) or Z value (SEM) at 2 hours | |
|---|---|---|---|---|---|---|
| | tramadol | gabapentin | Total Dose | Data % MPE | $Z_{mix}$ (SEM)[3] | $Z_{add}$ (SEM)[3] |
| Tramadol only | 50 | | | 3.77 | 94.47 (5.27)[2] | |
| | 75 | | | 20.62 | | |
| | 100 | | | 45.38 | | |
| | 125 | | | 74.29 | | |
| | 150 | | | 100 | | |
| 0.9:0.1 | 10.63 | 5.49 | 16.12 | 8.13 | 66.05* (5.30) | 127.50 (9.00) |
| | 21.26 | 10.99 | 32.24 | 29.46 | | |
| | 42.51 | 21.97 | 64.49 | 45.41 | | |
| | 85.02 | 43.95 | 128.97 | 65.21 | | |
| | 106.28 | 54.93 | 161.21 | 83.80 | | |
| 0.50:0.50 | 2.95 | 13.73 | 16.68 | 0.00 | Sub-additive | 266.98 |
| | 5.90 | 27.47 | 33.37 | 1.19 | | |
| | 11.80 | 54.94 | 66.74 | 2.26 | | |
| | 23.62 | 109.87 | 133.49 | 4.70 | | |
| | 47.24 | 219.74 | 266.98 | 11.62 | | |
| 0.1:0.9 | 9.45 | 395.50 | 404.95 | 16.98 | Sub-additive | 404.95 |
| Gabapentin only | | 100 | | 7.31 | 439.50 (60.50)[2] | |
| | | 250 | | 15.62 | | |
| | | 500 | | 54.26 | | |
| | | 750 | | 67.95 | | |
| | | 1000 | | 85.34 | | |

[1]SEM = standard error of the mean
[2]Represents ED$_{50}$ value of drug alone
[3]The determination of the total amount in the mixture that is required to produce a specified synergistic antiallodynic effect at the 50% dose level (that is, the ED$_{50mix}$ or Z$_{mix}$) and the corresponding total amount that would be expected under simple additivity (ED$_{50add}$ or Z$_{add}$).
*Synergistic combination

Example A3

Synergistic Effect of the Tramadol/Lamotrigine Composition

The interaction of selected, precise ratios based on a fraction of the ED$_{50}$ values of tramadol hydrochloride and lamotrigine for each ratio dosed in the Chung model are shown by the data in Table 3. The fixed ratio combination 1:3 revealed significant antiallodynic synergism (p<0.05).

TABLE 3

Tramadol:Lamotrigine Chung Model Data

| ED$_{50}$ value ratios (tramadol: lamotrigine) | TRAMADOL: LAMOTRIGINE DRUG COMBINATIONS Dose (mg/kg, p.o.) | | | Chung Model | ED$_{50}$ (SEM[1]) or Z value (SEM) at 2 hours | |
|---|---|---|---|---|---|---|
| | tramadol | Lamotrigine | Total Dose | Data % MPE | $Z_{mix}$ (SEM)[3] | $Z_{add}$ (SEM)[3] |
| Tramadol only | 50 | | | 3.77 | 94.47 (5.27)[2] | |
| | 75 | | | 20.62 | | |
| | 100 | | | 45.38 | | |
| | 125 | | | 74.29 | | |
| | 150 | | | 100 | | |
| 0.50:0.50 | 2.95 | 2.36 | 5.31 | 1.50 | 128.08 (76.0) | 83.79 (3.35) |
| | 5.90 | 4.73 | 10.63 | 6.16 | | |
| | 11.80 | 9.45 | 21.25 | 12.17 | | |
| | 23.62 | 18.88 | 42.50 | 19.48 | | |
| | 47.24 | 37.76 | 85.00 | 54.94 | | |
| 0.25:0.75 | 2.95 | 7.08 | 10.03 | 11.69 | 48.44* (2.24) | 79.40 (3.10) |
| | 5.90 | 14.16 | 20.07 | 26.42 | | |
| | 11.81 | 28.32 | 40.13 | 44.05 | | |
| | 23.62 | 56.65 | 80.27 | 66.03 | | |
| | 47.24 | 113.30 | 160.53 | 78.34 | | |
| 0.10:0.90 | 1.18 | 8.50 | 9.68 | 5.53 | 138.6 (17.7) | 77.0 (2.91) |
| | 2.36 | 16.99 | 19.35 | 12.56 | | |
| | 4.72 | 33.99 | 38.71 | 24.69 | | |
| | 9.45 | 67.98 | 77.43 | 42.39 | | |
| | 18.89 | 135.95 | 154.84 | 51.95 | | |

TABLE 3-continued

Tramadol:Lamotrigine Chung Model Data

| ED$_{50}$ value ratios (tramadol: lamotrigine) | TRAMADOL: LAMOTRIGINE DRUG COMBINATIONS Dose (mg/kg, p.o.) | | | Chung Model Data % MPE | ED$_{50}$ (SEM[1]) or Z value (SEM) at 2 hours | |
|---|---|---|---|---|---|---|
| | trama- dol | Lamo- trigine | Total Dose | | Z$_{mix}$ (SEM)[3] | Z$_{add}$ (SEM)[3] |
| Lamotrigine only | | 25 | | 5.48 | 75.53 (4.90)[2] | |
| | | 50 | | 21.95 | | |
| | | 75 | | 48.69 | | |
| | | 125 | | 75.09 | | |
| | | 150 | | 83.51 | | |

Figure 2:
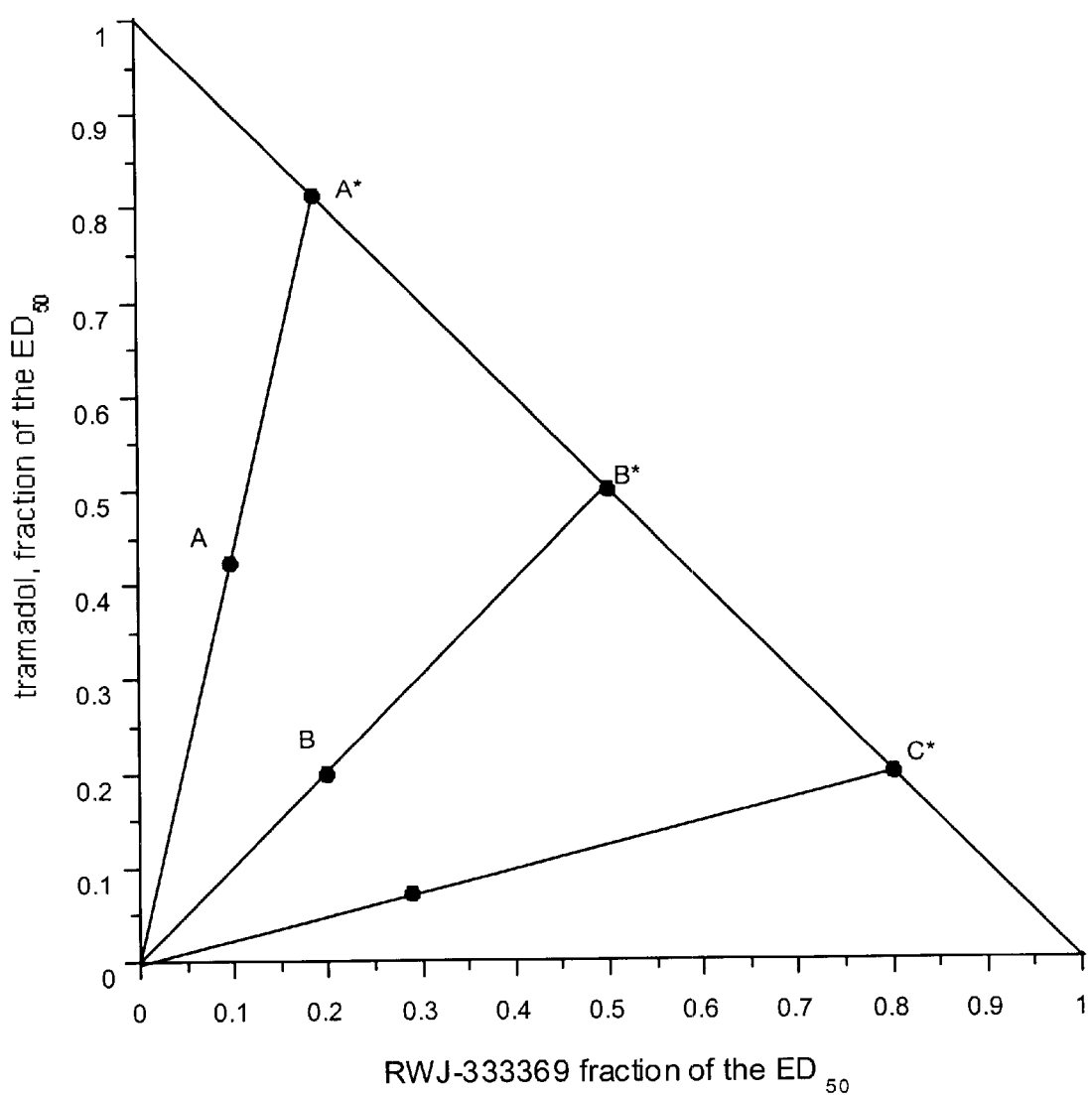
FIG. 2 is an isobologram showing the antiallodynic effect of certain combinations of tramadol hydrochloride and RWJ-333369 in rats using the Chung Model. The dose level for each component of each combination is expressed as the fraction of its $ED_{50}$ value.

[1]SEM = standard error of the mean
[2]Represents ED$_{50}$ value of drug alone
[3]The determination of the total amount in the mixture that is required to produce a specified synergistic antiallodynic effect at the 50% dose level (that is, the ED$_{50mix}$ or Z$_{mix}$) and the corresponding total amount that would be expected under simple additivity (ED$_{50add}$ or Z$_{add}$).
*Synergistic combination Example A4
Synergistic Effect of the Tramadol/RWJ-333369 Composition The interaction of selected, precise ratios based on a fraction of the ED$_{50}$ values of tramadol hydrochloride and RWJ-333369 for each ratio dosed in the Chung model are shown by the data in Table 4 and illustrated in the isobologram in FIG. 2.

In FIG. 2, the fraction of the ED$_{50}$ values for the individual drugs alone lie on their respective axes. For example, the ED$_{50}$ value of tramadol alone at 1 hour post-dosing was 48.56 mg/kg and is illustrated in FIG. 2 at the value of 1. The ED$_{50}$ value of RWJ-333369 alone at 1 hours post-dosing was 77.37 mg/kg and is illustrated in FIG. 2 at the value of 1. Therefore, the line joining the ED$_{50}$ value of the two separate drugs represents the calculated simple additivity of the antiallodynic effect at different ratios.

Accordingly, for each combination studied, the point at the asterisked letter (e.g., A*) represents the theoretical additive ED$_{50}$ value (Z$_{add}$) for a particular dose ratio. Further, the points labeled A, B and C represent the actual, experimentally determined fraction of the ED$_{50}$ values (Z$_{mix}$) for the tramadol hydrochloride and RWJ-333369 combinations in the ratios (of the ED$_{50}$ values) of 4:1, 1:1 and 1:4, respectively.

Each of the fixed ratio combinations tested revealed significant antiallodynic synergism (Student's t-test, p<0.05). Thus, the synergy was observed over a wide range of dose ratios.

TABLE 4

Tramadol:RWJ-333369 Chung Model Data

| ED$_{50}$ value ratios (tramadol: RWJ-333369 @ 1 hour) | TRAMADOL: RWJ-333369 DRUG COMBINATIONS Dose (mg/kg, p.o.) | | | Chung Model Data % MPE | ED$_{50}$ (SEM[1]) or Z value (SEM) at 1 hour | |
|---|---|---|---|---|---|---|
| | Trama- dol @ 1 hour | YKP- 509 @ 1 hour | Total Dose | | Z$_{mix}$ (SEM)[3] | Z$_{add}$ (SEM)[3] |
| Tramadol only | 10 | | | 16.79 | 48.56 (11.12)[2] | |
| | 30 | | | 25.70 | | |
| | 60 | | | 40.96 | | |
| | 90 | | | 73.61 | | |
| | 120 | | | 84.05 | | |
| 0.81:0.19 | 11.81 | 4.36 | 16.18 | 34.93 | 25.25 (1.09) | 53.54 (6.01) |
| | 23.62 | 8.75 | 32.37 | 58.17 | | |
| | 47.24 | 17.50 | 64.74 | 82.11 | | |
| | 94.47 | 35.00 | 129.47 | 100 | | |
| 0.50:0.50 | 3.04 | 4.84 | 7.88 | 15.31 | 28.14 (4.04) | 62.55 (7.39) |
| | 6.07 | 9.67 | 15.74 | 27.47 | | |
| | 12.14 | 19.34 | 31.48 | 45.77 | | |
| | 24.28 | 38.69 | 62.97 | 81.96 | | |
| 0.20:0.80 | 0.61 | 3.87 | 4.48 | 10.40 | 25.93 (0.615) | 72.35 (8.88) |
| | 1.21 | 7.74 | 8.95 | 24.77 | | |
| | 2.43 | 15.48 | 17.90 | 40.01 | | |
| | 4.86 | 30.95 | 35.81 | 58.42 | | |
| | 9.71 | 61.90 | 71.61 | 74.13 | | |
| RWJ- 333369 only | | 30 | | 5.57 | 77.37 (5.09)[2] | |
| | | 45 | | 23.01 | | |
| | | 60 | | 30.43 | | |
| | | 75 | | 54.54 | | |
| | | 90 | | 57.01 | | |

[1]SEM = standard error of the mean
[2]Represents ED$_{50}$ value of drug alone
[3]The determination of the total amount in the mixture that is required to produce a specified synergistic antiallodynic effect at the 50% dose level (that is, the ED$_{50mix}$ or Z$_{mix}$) and the corresponding total amount that would be expected under simple additivity (ED$_{50add}$ or Z$_{add}$).

General Method B
Procedure for Testing the Antinociceptive Effect of the Composition The procedure used to detect and compare the synergistic effect of the composition of the present invention for which there is a good correlation with human efficacy for the treatment of pain is the procedure, with minor modifications, for the measurement of antinociception found in the Mouse Hot Plate Model (Eddy and Leimbach, *J. Pharmacol. Exp. Ther.*, 1953, 107, 385–393; and O'Callaghan and Holtzman, *J. Pharmacol. Exp. Ther.*, 1975, 192, 497–505). Mice were placed on a heated surface (48° C.) and the time interval (seconds) between placement and a shaking, licking, or tucking of the hind paw was recorded as the predrug latency response. This same procedure was repeated at various times after the test drug was administered p.o., 10 mL/kg.

Within a certain time after the oral administration of tramadol hydrochloride, topiramate, or a combination of tramadol hydrochloride and topiramate, testing was performed. Each mouse was used in the evaluation of only a single dose of a single dose-ratio. The 48° C. Mouse Hot Plate was used to calculate the % maximal possible effect (% MPE) according to the formula:

$$\% \text{ MPE} = \left( \frac{(\text{Test Latency} - \text{Predrug Latency})}{(\text{Cutoff time} - \text{Predrug Latency})} \right) \times 100$$

The analysis of possible synergistic effect at each fixed ratio was determined as described by Tallarida, et al., above.

Preparation of the Composition Doses of Tramadol Hydrochloride and Topiramate

The dosing materials were all prepared in the vehicle, a suspension of 0.5% hydroxypropyl methylcellulose in distilled water; and drug weights were calculated as the free base. The tramadol solution was prepared first, and the appropriate volume of this solution was added to a neat amount of topiramate to give the final dosing suspension. Drug weights were calculated as the free base. The necessary doses were prepared separately and dosed orally in a volume of 10 mL/kg per mouse.

Example B1
Synergistic Effect of the Tramadol/Topiramate Composition

Figure 3:
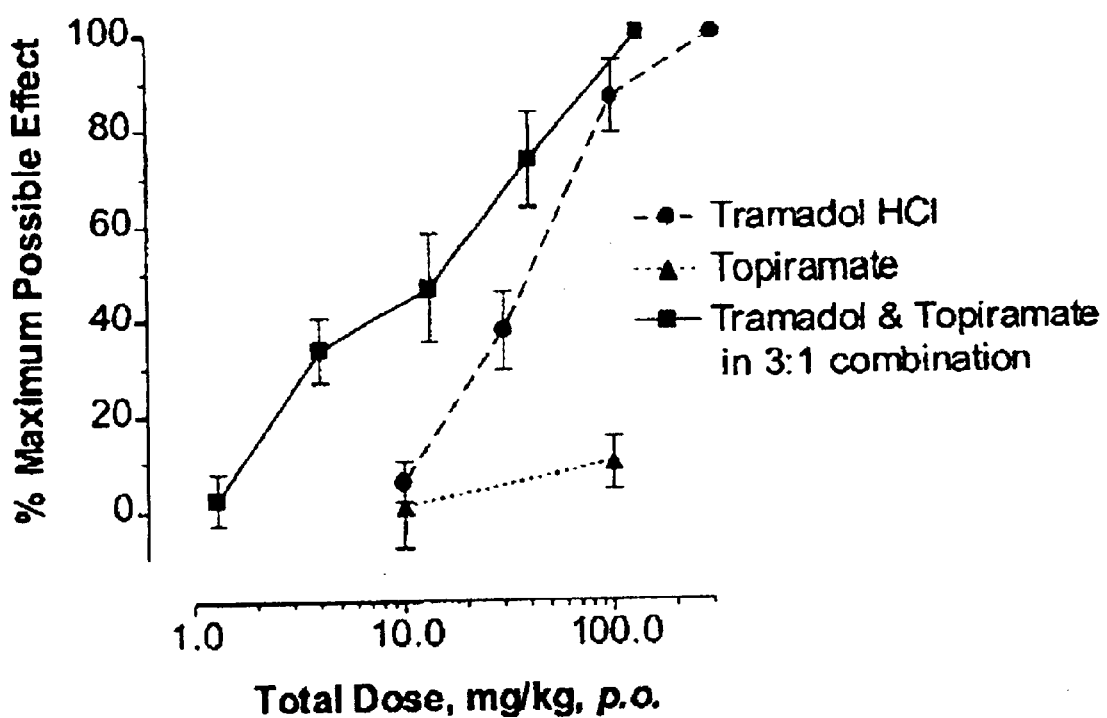
FIG. 3 are dose response curves showing the antinociceptive effect of certain combinations of tramadol hydrochloride and topiramate in mice using the Mouse Hot Plate Model.

Dose-response studies were conducted for tramadol, for topiramate, and for a 3:1 ratio of tramadol:topiramate combined. Tramadol alone and the combination tested exhibited a dose-dependent antinociceptive effect (Table 5, FIG. 3). Full antinociceptive effect was observed at the higher doses for tramadol and the combination tramadol:topiramate. At a 3:1 ratio, the combination of tramadol and topiramate, administered orally, exhibited synergy in the production of an antinociceptive effect in the 48° C. Mouse Hot Plate test. This study confirms the broad synergy of tramadol:anticonvulsant combinations in painful conditions.

TABLE 5

Tramadol:Topiramate Mouse Hot Plate Model Data

| Ratios | Tramadol:Topiramate Drug Combinations Dose (mg/kg p.o.) | | | % Maximal Possible Effect | $ED_{50}$ (SEM) at 1.5 Hours |
|---|---|---|---|---|---|
| (Tramadol:Topiramate) | Tramadol | Topiramate | Total Dose | | |
| Tramadol only | 10 | | 10 | 5.83 | 35.1[b] (1.59) |
| | 30 | | 30 | 37.74 | |
| | 100 | | 100 | 86.62 | |
| | 300 | | 300 | 100 | |
| 0.75:0.25 | 1 | 0.3 | 1.3 | 2.40 | 9.54 (1.42) |
| | 3 | 1.0 | 4.0 | 33.46 | |
| | 10 | 3.3 | 13.3 | 46.82 | |
| | 30 | 10.0 | 40.0 | 73.66 | |
| | 100 | 33.3 | 133.3 | 100 | |
| Topiramate only | | 10 | 10 | 0.82 | |
| | | 30 | 30 | 9.71 | |

[a]SEM = standard error of the mean
[b]Represents $ED_{50}$ value of drug alone

We claim:

1. A pharmaceutical composition comprising a synergistic combination of a tramadol material and topiramate, wherein the tramadol material and topiramate are present in a ratio based on a fraction of their respective $ED_{50}$ values, which ratio is from about 1:1 to about 300:1 or from about 1:1 to about 1:300.

2. The pharmaceutical composition of claim 1, wherein the tramadol material and topiramate are present in a ratio based on a fraction of their respective $ED_{50}$ values, which ratio is from about 1:1 to about 100:1 or from about 1:1 to about 1:100.

3. The pharmaceutical composition of claim 1, wherein the tramadol material and topiramate are present in a ratio based on a fraction of their respective $ED_{50}$ values, which ratio is from about 1:1 to about 30:1 or from about 1:1 to about 1:30.

4. The pharmaceutical composition of claim 1, wherein the tramadol material is selected from the group consisting of (1R,2R)-2-[(dimethylamino)methyl]-1-(3-methoxyphenyl)-cyclohexanol, (1S,2S)-2-[(dimethylamino)methyl]-1-(3-methoxyphenyl)-cyclohexanol, a racemic mixture of (1R,2R)-2-[(dimethylamino)methyl]-1-(3-methoxyphenyl)-cyclohexanol and (1S,2S)-2-[(dimethylamino)methyl]-1-(3-methoxyphenyl)-cyclohexanol, a N-oxide derivative of (1R,2R)-2-[(dimethylamino)methyl]-1-(3-methoxyphenyl)-cyclohexanol, a N-oxide derivative of (1S,2S)-2-[(dimethylamino)methyl]-1-(3-methoxyphenyl)-cyclohexanol, racemic mixtures of a N-oxide derivative of (1R,2R)-2-[(dimethylamino)methyl]-1-(3-methoxyphenyl)-cyclohexanol and a N-oxide derivative of (1S,2S)-2-[(dimethylamino)methyl]-1-(3-methoxyphenyl)-cyclohexanol, an O-desmethyl derivative of (1R,2R)-2-[(dimethylamino)methyl]-1-(3-methoxyphenyl)-cyclohexanol, an O-desmethyl derivative of (1S,2S)-2-[(dimethylamino)methyl]-1-(3-methoxyphenyl)-cyclohexanol, racemic mixtures of an O-desmethyl derivative of (1R,2R)-2-[(dimethylamino)methyl]-1-(3-methoxyphenyl)-cyclohexanol and an O-desmethyl derivative of (1S,2S)-2-[(dimethylamino)methyl]-1-(3-methoxyphenyl)-cyclohexanol, solvates, polymorphs and pharmaceutically acceptable salts thereof.

5. The pharmaceutical composition of claim 4, wherein the tramadol material is tramadol hydrochloride.

6. The pharmaceutical composition of claim 5, wherein the tramadol hydrochloride is racemic.

7. The pharmaceutical composition of claim 6, wherein the tramadol hydrochloride is an enantiomer.

8. The pharmaceutical composition of claim 4, wherein the tramadol material is O-desmethyl tramadol.

9. The pharmaceutical composition of claim 8, wherein the O-desmethyl tramadol is racemic.

10. The pharmaceutical composition of claim 9, wherein the O-desmethyl tramadol is an enantiomer.

11. The pharmaceutical composition of claim 1, further comprising a pharmaceutically acceptable carrier.

* * * * *